(12) United States Patent
Cohen

(10) Patent No.: US 6,506,387 B1
(45) Date of Patent: Jan. 14, 2003

(54) METHOD FOR PREPARING ALOIN BY EXTRACTION

(75) Inventor: Avraham Cohen, Tel Aviv (IL)

(73) Assignee: Paxa N.V., The Hague (NL)

( * ) Notice: Subject to any disclaimer, the term of this patent is extended or adjusted under 35 U.S.C. 154(b) by 0 days.

(21) Appl. No.: 09/701,955

(22) PCT Filed: Apr. 20, 1999

(86) PCT No.: PCT/IB99/00771

§ 371 (c)(1),
(2), (4) Date: Feb. 16, 2001

(87) PCT Pub. No.: WO00/66601

PCT Pub. Date: Nov. 9, 2000

(51) Int. Cl.[7] .................. A61K 35/78; A61K 31/715
(52) U.S. Cl. .................. 424/195.1; 424/725; 536/18.5; 536/123.1; 536/127; 536/128; 514/54; 514/862; 514/863; 514/886; 435/29; 435/32
(58) Field of Search .................. 424/195.1, 725; 435/29, 32; 514/862, 863, 886, 54; 536/18.5, 123.1, 127, 128

(56) References Cited

U.S. PATENT DOCUMENTS

| 4,602,004 A | | 7/1986 | Cohen | |
|---|---|---|---|---|
| 4,670,263 A | * | 6/1987 | Noorlander | 424/195.1 |
| 4,957,907 A | * | 9/1990 | McAnalley | 514/54 |
| 4,966,892 A | * | 10/1990 | McAnalley | 514/54 |
| 5,330,756 A | * | 7/1994 | Steuart et al. | 424/405 |
| 6,290,964 B1 | * | 9/2001 | Shupe et al. | 424/195.1 |
| 6,309,675 B1 | * | 10/2001 | Sobczak | 424/738 |

FOREIGN PATENT DOCUMENTS

| EP | 0 374 890 A1 | 6/1990 |
|---|---|---|
| WO | WO 87/00052 | 1/1987 |

* cited by examiner

*Primary Examiner*—Samuel Barts
*Assistant Examiner*—Devesh Khare
(74) *Attorney, Agent, or Firm*—Clifford W. Browning; Woodard, Emhardt, Naughton, Moriarty & McNett LLP

(57) ABSTRACT

The invention concerns a method for preparing aloin which consists in extracting from a substance containing aloe, in particular the yellow sap of aloe or a derived product, in the presence of an aliphatic diol or triol with low molecular weight, for instance glycerol or a glycol, followed by a purification by crystallization in an alcohol. The invention is useful for industrial preparation of aloin.

10 Claims, No Drawings

METHOD FOR PREPARING ALOIN BY EXTRACTION

BACKGROUND OF THE INVENTION

The present invention refers to a method for the preparation of aloin, more particularly to a method for extracting aloin from aloe juice, or of derived products that is of industrial utility and gives a final product of good purity in satisfactory yields.

Aloin is a natural substance that can be obtained in a classical way by extraction starting with aloe gel. It is a highly interesting substance owing to the pharmacological properties of several derivatives that are of utility in diverse medications. The rhein for instance, which can be obtained from aloin, has the properties of a laxative, antirheumatic, antiarthrosic, and antiarthritic useful in therapy.

The methods that have most commonly been used over numerous years, generally consist in an extraction starting from hard gum, that is, from a hardened residue obtained when concentrating the juice by simple heating in the open air under atmospheric pressure. The extraction yields aloin that can be purified by recrystallization in an appropriate solvent.

The patent EP-A-374 890 describes a method of extraction of the aloin and aloe emodin from plants or plant extracts with a hydrophilic solvent, filtration, and evaporation to obtain a syrup which is then subjected to several extractions, then a recrystallization. The solvents used are alcohols, acetone, ethyl acetate, and water.

The usual chemical designation of aloin is 10-glucopyranosyl-1,8-dihydroxy-3-hydroxymethyl-9(10H)-anthracenone. Aloin exists in the form of two isomers, A and B, which differ by the position of the glucose group at the anthrone base, their proportions being susceptible to vary depending on the origin of the plants and on the extraction methods used. An aloin with a high content of isomer A is generally preferred.

SUMMARY OF THE INVENTION

Studies and tests performed by applicant have shown that it was possible to significantly improve the classical extraction method by using an additive that facilitates the extraction and subsequently allows the purification to be improved. In particular, the method according to the invention yields an improved selectivity of extraction and considerable decrease in the amounts of solvent used in the purification under the conditions under which the method is practiced on an industrial scale.

The method of preparing aloin according to the present invention essentially comprises an extraction of an exudate of aloe, particularly of the yellow juice of aloe, for instance of aloe barbadensis or also aloe capensis, or a derived product, in the presence of an aliphatic diol or triol of low molecular weight, followed by a purification by crystallization.

According to a preferred embodiment, the aliphatic diol or triol of low molecular weight is added in a first step to the yellow aloe juice, and a concentration is performed, then an extraction is realized in a second step. This first step can of course be realized with an aloin-containing derivative of the juice such as hard gum, but it is preferred to directly use the yellow juice, which corresponds to a less degraded substance.

The extraction is followed by a recrystallization from an alcohol that can be selected among ethanol, n-propanol, isopropanol, n-butanol, tert-butanol, and isobutanol.

According to the present invention, the expression "aliphatic diol or triol of low molecular weight" designates a diol or triol with no more than 15 carbon atoms in its carbon chain, preferably no more than ten carbon atoms. The aliphatic diol or triol of low molecular weight used in the invention can for instance be a glycol or glycerol. The glycol is preferably selected from ethylene glycol, diethylene glycol, propylene glycol, butylene glycol, tripropylene glycol, and triethylene glycol. The aliphatic diol or triol is used in amounts between 5 and 25% by weight, preferably between 7 and 15%, relative to the weight of yellow juice used as the starting material.

As indicated above, after concentrating the yellow juice in the presence of aliphatic diol or triol one performs the extraction with a solvent selected preferably among ethyl acetate and acetone.

For satisfactory yields, the extraction solvent selected is important. Thus, comparative tests have shown that the overall yield relative to the aloin present in the starting material is about 50% when ethyl acetate is used, while the extraction is poor, that is, below 10%, when chloroform or petrol ether are used. The purity of the product after extraction, that is, its aloin content, also is below 10% when the ethyl acetate or acetone are replaced by chloroform.

The method of the invention leads to an important improvement in extraction selectivity over the classical methods, since the aloin content of the extracted product prior to purification is of the order of 60%, while it is around 50% in the case of an extraction by a usual method.

The quality of the aloin obtained, and its overall yield, can be optimized when the water content is controlled during purification by recrystallization from an alcohol. Thus, according to an advantageous feature of the invention, the purification by recrystallation is performed in the presence of 0.5 to 5%, preferably 0.5 to 2%, by weight of water relative to the medium's total weight. The amount of water can be adjusted as usual, either by adding water when its content is low, or by azeotropic distillation when it is high.

The method according to the present invention allows a product to be obtained which has an aloin content of over 80%, generally between 85 and 90%, and even higher than 90%, when the water content during purification is controlled. Under the conditions that are applicable when realizing the method on an industrial scale, the overall yield relative to the aloin present in the starting material (yellow aloe juice or derived product) is higher than 50%.

Another advantage of the method of the invention is that of allowing an important reduction in the amount of alcohol used in the purification step following extraction. Thus, in the case of a recrystallization in isobutanol, the amount of alcohol is between 10 and 20 volumes per volume of aloin present in the medium, as against 40 to 60 volumes in the usual methods.

The aloin obtained by the method of the invention can be used to prepare medications on the basis of rhein or of derivatives that are used in treating arthrosis, arthritis, and various inflammations.

The following examples illustrate the invention in greater detail without limiting its scope. Unless mentioned othewise, the parts and percentages are given in terms of weight.

DETAILED DESCRIPTION OF THE PREFERRED EMBODIMENT

EXAMPLE NO. 1

As a comparative example, aloin is prepared by the method indicated hereafter.

In an evaporating flask of 1 L, 200 g of yellow juice of aloe vera are concentrated at a pressure of about 4(103 Pa on a water bath heated to about 55° C. After elimination of 75% of the water the concentrate is taken up in 600 ml of ethyl acetate at a temperature between 55 and 60° C. while vigorously stirring for 30 min.

After decanting, the organic supernatent is withdrawn, and the aqueous residue is thrice extracted with ethyl acetate at a temperature between 50 and 60° C. The extracts are combined and concentrated in vacuum while maintaining the temperature between 45 and 50° C.

One thus obtains a brown-orange-colored solid having an aloin content of about 45–50% which is redissolved in 640 ml of isobutanol at 70° C. (that is, 40 volumes of isobutanol relative to the aloin present).

The isobutanol solution is cooled to 5° C. and kept for about four hours at this temperature.

The aloin that crystallizes is collected by filtration on a Büchner funnel, while the filter cake is washed with 20 ml of isobutanol.

After drying one thus obtains a product in the form of a yellow-brown powder having an aloin content of 86% as determined by chromatography (HPLC).

The yield of pure aloin relative to the aloin in the yellow juice used as the starting material is 40%.

EXAMPLE NO. 2

The method according to the present invention follows the principle of extraction described in Example No. 1, but modified as indicated hereafter.

In an evaporating flask of 1 L, 200 g of the yellow juice of aloe vera identical with that used in Example No. 1 but to which 20 g of ethylene glycol have been added in advance are placed and concentrated at a pressure of about 4(103 Pa. After elimination of 75% of the water the concentrate is taken up in 600 ml of ethyl acetate under the same conditions as in Example No. 1.

After decanting, the organic supernatant is withdrawn, and the aqueous residue is thrice extracted with ethyl acetate, then the extracts are combined and concentrated in vacuum while maintaining the temperature between 45 and 50° C.

One thus obtains an oily, brown product having an aloin content of about 55–60% which is redissolved in 240 ml of isobutanol at 70° C. (that is, 15 volumes of isobutanol relative to the aloin present).

The isobutanol solution is cooled to 5° C. and kept for about four hours at this temperature, as in Example No. 1.

The aloin that crystallizes is collected by filtration on a Büchner funnel, and after washing with 20 ml of isobutanol and drying one thus obtains a product in the form of a yellow-brown powder having an aloin content of 87% as determined by chromatography (HPLC). The ratio of aloin A to aloin B is about 3/1.

The yield of pure aloin relative of the aloin in the yellow juice used as the starting material is 53%.

EXAMPLE NO. 3

One proceeds as indicated in Example No. 2, but replaces the ethylene glycol with the same amount of diethylene glycol.

One thus obtains an 87% pure aloin in a yield of 52%.

EXAMPLE NO. 4

One proceeds as indicated in Example No. 2, but replaces the ethylene glycol with the same amount of glycerol.

One thus obtains a product having an aloin content of 87%, in an overall yield of 48%.

EXAMPLE NO. 5

One proceeds as indicated in Example No. 2, but after the extraction with ethyl acetate, the extract obtained is taken up in 240 ml of isobutanol while the amount of water is adjusted to 1% relative to the medium's total weight.

One thus obtains a product having an aloin content of 90%, in an overall yield of 56%.

I claim:

1. Method for preparing aloin from yellow sap of aloe or a derived product, by extraction and purification, characterized in that one performs the extraction of the yellow sap of aloe or of the derived product in the presence of an aliphatic diol or triol of low molecular weight.

2. Method according to claim 1, characterized in that the aliphatic diol or triol of low molecular weight is added to the yellow sap of aloe, then a concentration is performed prior to extraction.

3. Method according to claim 1, characterized in that the extraction is followed by a recrystallization in an alcohol.

4. Method according to claim 3, characterized in that the alcohol is selected from among ethanol, n-propanol, isopropanol, n-butanol, tert-butanol, and isobutanol.

5. Method according to claim 3, characterized in that the recrystallization is performed in the presence of 0.5 to 5% by weight of water relative to the medium's total weight.

6. Method according to claim 1, characterized in that the extraction is performed on the sap of aloe vera, aloe barbadensis or aloe capensis.

7. Method according to claim 1, characterized in that the aliphatic diol or triol of low molecular weight is a glycol or glycerol.

8. Method according to claim 7, characterized in that the glycol is selected from among ethylene glycol, diethylene glycol, propylene glycol, butylene glycol, tripropylene glycol, and triethylene glycol.

9. Method according to claim 7, characterized in that the amount of aliphatic diol or triol of low molecular weight is between 5 and 25% by weight relative to the weight of yellow sap.

10. Method according to claim 1, characterized in that the extraction is performed with a solvent selected among ethyl acetate and acetone.

* * * * *